United States Patent [19]

Record et al.

[11] Patent Number: 5,717,070
[45] Date of Patent: Feb. 10, 1998

[54] FILAMENTOUS FUNGUS PROTEINS FOR BINDING AND TRANSPORTING LIPIDS, METHOD FOR PREPARING THEM AND THEIR APPLICATIONS

[75] Inventors: Eric Record; Laurence Lesage, both of Marseilles; Didier Marion; Bernard Cahagnier, both of Nantes; Daniel Richard-Molard, Orvault; Marcel Asther, La Ciotat, all of France

[73] Assignee: Institut National de la Recherche Agronomique-Inra, Paris, France

[21] Appl. No.: 318,699

[22] PCT Filed: Feb. 10, 1994

[86] PCT No.: PCT/FR94/00151

§ 371 Date: Jan. 23, 1995

§ 102(e) Date: Jan. 23, 1995

[87] PCT Pub. No.: WO94/18240

PCT Pub. Date: Aug. 18, 1994

[30] Foreign Application Priority Data

Feb. 11, 1993 [FR] France ........................... 93 01518

[51] Int. Cl.⁶ .................. C07K 1/00; C12N 1/00; A61K 38/00
[52] U.S. Cl. ............... 530/359; 530/324; 530/412; 530/417; 530/418; 530/427; 530/824; 435/242; 435/254.1; 435/254.3; 435/254.5; 435/254.8; 435/255.1; 435/261; 435/911; 435/913; 435/939; 424/78.03; 424/450; 514/7; 514/12
[58] Field of Search ..................... 530/359, 324, 530/412, 417, 418, 427, 824; 435/7.31, 70.1, 242, 254.1, 254.3, 254.5, 254.8, 255.1, 261, 911, 913, 939; 424/450, 78.03; 514/7, 12

[56] References Cited

FOREIGN PATENT DOCUMENTS

| 0 504 043 | 9/1962 | European Pat. Off. . |
| 0504043 | 9/1992 | European Pat. Off. . |
| 3815473 | 11/1989 | Germany . |
| A 63 074 491 | 4/1988 | Japan . |
| 5056776 | 3/1993 | Japan . |

OTHER PUBLICATIONS

De Scheemaeker et al, *Developments in Plant Biology*, vol. 9, pp. 303–306, 1984.
Groudin et al, *Int. J. Biochem.*, vol. 22, No. 1, pp. 93–98, 1990.
Basu et al, *Biochimica et Biophysica Acta*, vol. 1126, No. 3, pp. 286–290, 1992.
Tai et al., *J. Biol. Chem.*, vol. 259, No. 19, pp. 12178–12183, Oct. 10, 1984.
Record et al, *Biochemica et Biophysica Acta*, vol. 1256, No. 1, pp. 18–24, Apr. 28, 1995.
Basu et al., "Purification of a Phosphatidylinositol/Phosphatidylcholine Transfer Protein From *Neurospora Crassa*", *Biochimica et Biophysica Acta*, vol. 1126, No. 3, (1992) Amsterdam NL, pp. 286–290.
Grondin et al., "Purification and Characterization of a Novel Phospholipid Transfer Protein From Filamentous Fungi", *International Journal of Biochemistry*, vol. 22, No. 1, 1990 Oxford GB, pp. 93–98.
De Scheemaeker et al., "Comparison Between Phospholipid Transfer Proteins in Two Filamentous Fungi", *Developments in Plant Biology*, vol. 9, (1984) Amsterdam NL pp. 303–306.
Yamada, "Lipid transfer proteins in palnts and microorganisms", vol. 33, No. 1, Jan. 1992, Tokyo, Japan, pp. 1–6.

*Primary Examiner*—Cecilia J. Tsang
*Assistant Examiner*—Abdel A. Mohamed
*Attorney, Agent, or Firm*—Fitch, Even, Tabin & Flannery

[57] ABSTRACT

The present invention is directed to a family of phospholipid binding and transporting proteins, a method for preparing same from fungi, and their use in cosmeticology, the agrifoodstuffs industry and pharmacology Phospholipid proteins are capable of binding, transporting and/or rearranging lipids between membranes, optionally in combination with active principles. Furthermore, the phospholipid proteins are hydrophobic and acidic, have a molecular weight of under 50 kDa, and may be prepared from a non-toxic filamentous fungus capable of developing on a lipid-enriched medium, particularly from raw extracts of fungi.

17 Claims, 8 Drawing Sheets

PURIFICATION STEPS

•• 1st STEP (COMMON TO THE 2 PLTPs):

GEL FILTRATION ------- 2 PHOSPHOLIPID TRANSFER
G75                    ACTIVITY PEAKS

PEAK 1 ←                           → PEAK 2

•• 2nd STEP:

DEAE                               DEAE
GRADIENT 200-700 mM                GRADIENT 100-500 mM

•• 3rd STEP:

SEPHACRYL S 400                    MONO Q
                                   GRADIENT OF 100-500 mM

•• ELECTROPHORESIS:

30 kDa PLTP                        18 kDa PLTP

FIGURE 6

FILAMENTOUS FUNGUS PROTEINS FOR BINDING AND TRANSPORTING LIPIDS, METHOD FOR PREPARING THEM AND THEIR APPLICATIONS

BACKGROUND OF THE INVENTION

The present invention relates to a family of lipid binding and transporting proteins, to the method for preparing them from fungi, as well as to their applications in cosmetology, in the agri-foodstuffs industry and in the pharmaceutical field.

The present invention also relates to the crude fungal extracts containing such proteins and to their applications in the pharmaceutical and cosmetological fields and in the agri-foodstuffs field.

Phospholipid transfer proteins (PLTP) have been isolated from fungi such as *Mucor mucedo*, *Aspergillus ochraceus* or *Neurospora crassa* (Intern. J. Biochem., 1990, 22, 1, 93–98; Develop. Plant Biol., 1984, 9, 303–306; BBA, 1992, 1126, 3, 286–290), from fungal cultures produced on synthetic media using glucose as carbon source. However, the culture of fungi on such synthetic media makes it possible to obtain only small quantities of PLTP (very low yields); consequently, such cultural methods are not industrially applicable.

The need for a method for preparing, in large quantities, lipid binding and transporting proteins capable of ensuring the intermembrane transport of lipids and the preparation of proteins permitting a selective transport of certain phospholipids [(phosphatidylglycerol (PG), phosphatidylinositol (PI)] is critically felt, especially for improving the efficacy of action of liposomes, whose applications are numerous both in the drug field and in cosmetology and generally for producing modified biomembranes.

SUMMARY OF THE INVENTION

Consequently, the present invention set itself the aim of providing phospholipid transfer proteins (PLTP) capable of being produced in large quantities by filamentous fungi and capable of ensuring selective intermembrane transport of lipids (phospholipids and sterols) and active ingredients; such proteins are more suitable for the requirements of practical use, especially in that they make it possible to improve the biological and surfactant activities of the membranes.

Indeed, membranes are the seat of numerous functions in the development of living organisms (cellular recognition and exchange, respiration, excretion and the like) and constitute a barrier which is difficult to modify; yet, biomembrane engineering involves the modification of their composition and their organization.

The subject of the present invention is a method for preparing phospholipid transfer proteins (PLTP) from non-toxic filamentous fungi of the type comprising the preparation a crude extract, the separation of the proteins from the said extract and the purification of the said proteins, which method is characterized in that the said fungi are cultured in a phospholipid-rich medium.

BRIEF DESCRIPTION OF THE DRAWINGS

FIG. 6 shows the steps in the purification of crude extract.

DETAILED DESCRIPTION OF THE PREFERRED EMBODIMENT

Figure 1:
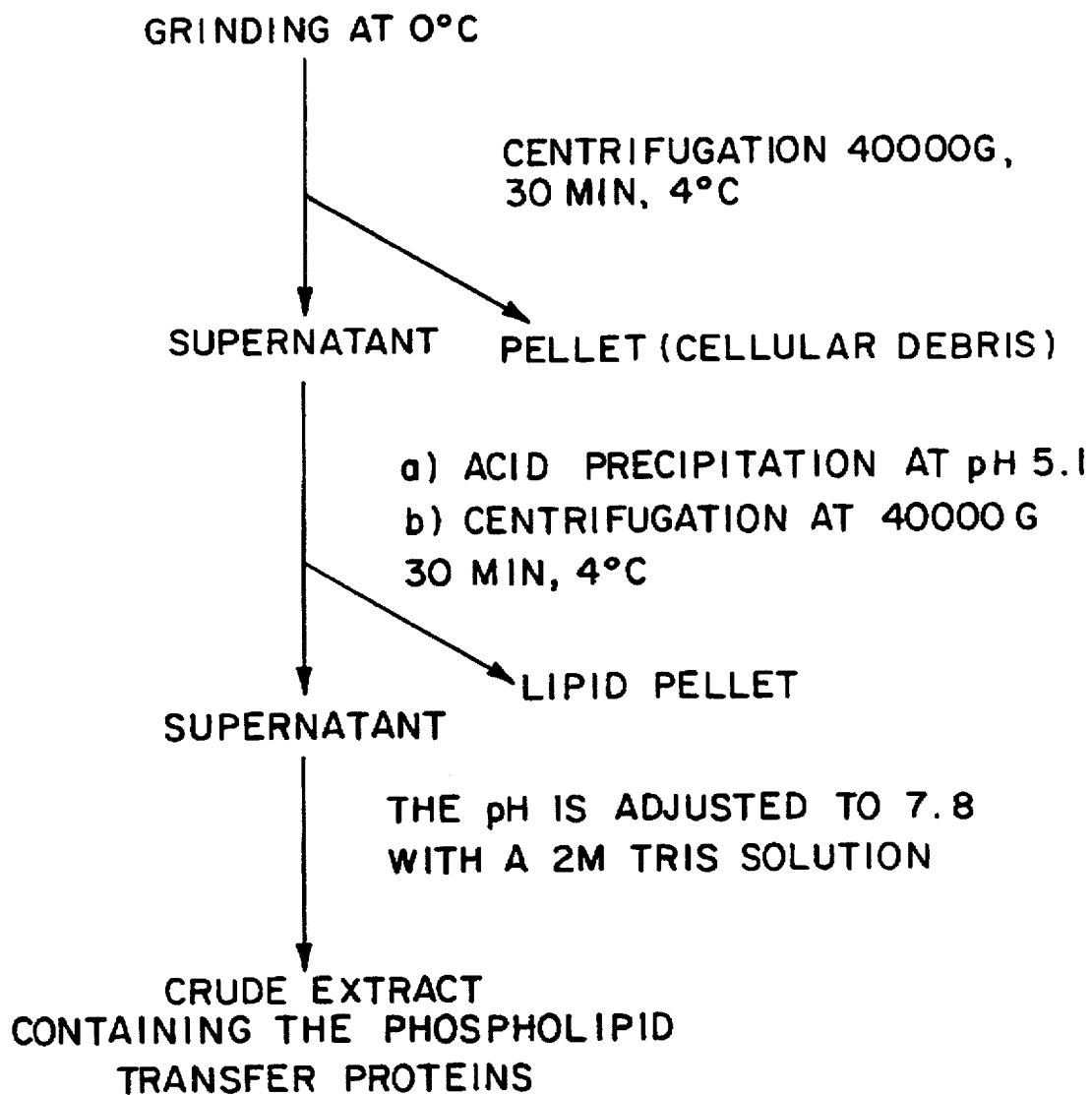
FIG. 1 shows the steps in the preparation of crude extract.

According to an advantageous embodiment of the said method, the said phospholipid-rich culture medium comprises between 3 and 20 g/l of phospholipids.

According to another advantageous embodiment of the said method, it comprises:

(1) the preparation of a crude extract at an essentially neutral pH by:
   (a) culturing the said fungi in the said phospholipid-rich medium until a sufficient quantity of mycelium is obtained,
   (b) grinding the said mycelia in an extraction buffer at neutral pH,
   (c) separating the crude extract containing the lipid binding and transfer proteins from the said ground product, by
      centrifugation of the said ground product at a speed above 20,000 g (first centrifugation) and recovery of the supernatant S1,
      acid precipitation of the supernatant S1, followed by a centrifugation at a speed above 20,000 g (second centrifugation) and recovery of the supernatant S2,
   (d) preparing the crude extract containing the said lipid binding and transfer proteins from the supernatant S2, buffered to an essentially neutral pH,
(2) the concentration of the proteins by ultrafiltration,
(3) the separation of the fractions having a lipid binding and transfer activity using a gel, filtration and selection of the active fractions by measuring the lipid binding and transfer activity, and
(4) the purification of the proteins of the various fractions selected, by a series of chromatographic steps,
which obtained proteins are capable of ensuring the intermembrane binding, transport and/or rearrangement of lipids, optionally combined with active ingredients, are hydrophobic and acidic, and have a molecular weight of less than 50 kDa.

According to another advantageous embodiment of the said method, the said filamentous fungi are selected from the group which comprises the Ascomycetes chosen from *Aspergillus candidus*, *A. flavipes*, *A. fumigatus*, *A. giganteus*, *A. niger*, *A. ochraceus*, *A. oryzae*, *A. terreus*, *A. versicolor*, *A. wentii*, *Penicillium roquefortii* and *Eurotium chevalieri*, the Zygomycetes chosen from *Mucor mucedo* and *Rhizopus stolonifer* and the Basidiomycetes selected from the species *Phanerochaete chrysosporium*.

For the purposes of the present invention, these various groups include both mother strains and variants or mutants of these mother strains.

The various strains mentioned above with no limitation being implied are in particular deposited with collections as specified in the table below:

| Strains | Strain no. and collection where the strain was deposited | |
|---|---|---|
| *Aspergillus candidus* | no. 2.12 | LMTC |
| *A. flavipes* | no. 2.6 | LMTC |
| *A. fumigatus* | no. 978 | MUCL |
| *A. giganteus* | no. 2.8 | LMTC |
| *A. niger* | no. 2.7 | LMTC |
| *A. ochraceus* | no. 14207 | MUCL |
| *A. oryzae* | no. 2.14 | LMTC |
| *A. terreus* | no. 21932 | MUCL |
| *A. versicolor* | no. 2.1 | LMTC |
| *A. wentii* | no. 1043 | MUCL |
| *Penicillium roquefortii* | no. 29083 | MUCL |
| *Eurotium chevalieri* | no. 2.10 | LMTC |
| *Mucor mucedo* | no. 18552 | MUCL |
| *Rhizopus stolonifer* | no. 5.4 | LMTC |
| *Phanerochaete chrysosporium* | no. F17-67 | LBCF |

These various strains are accessible, depending on the cases, at the INRA Laboratory of Cereal Microbiology and Technology (LMTC) at Nantes, at the Fungus Culture Collection of the Catholic University of Louvain (MUCL, Belgium) and at the INRA Laboratory of Filamentous Fungus Biotechnology (LBCF) at Marseille.

According to still another advantageous embodiment of the said method, step (a) includes, in addition:
culturing the said fungi on a sporulation medium,
incubating for 2 to 13 days until a sufficient quantity of spores is obtained,
culturing the said spores on the said phospholipid-rich culture medium, and
incubating until a sufficient quantity of mycelium is obtained.

According to an advantageous feature of this embodiment, the sporulation medium advantageously consists of moistened whole maize grains.

According to another advantageous embodiment of the said method, the acid precipitation of step (c) is performed at pH 5.1.

The acid precipitation, preferably at pH 5.1, offers the advantage of freeing the lipid transfer proteins of soluble lipoprotein complexes which interfere with the phospholipid transfer assays. It is in addition necessary to adjust the pH of the crude extract to neutral pH so as to stabilize the said proteins.

According to still another advantageous embodiment of the said method, steps (b) and (c) are performed at cold temperature.

According to another advantageous embodiment of the said method, the filamentous fungus is a filamentous fungus strain *A. oryzae*.

According to an advantageous feature of this embodiment, step (4) provides a protein having a lipid transfer activity and having a molecular weight of about 19 kDa.

According to another advantageous feature of this embodiment, step (4) provides a protein having a lipid transfer activity and having a molecular weight of about 30 kDa.

Unexpectedly, the use of phospholipids as carbon source specifically increases the endoplasmic reticulum of the cells (×10–20) (site of synthesis of phospholipids) and therefore the synthesis of the transfer proteins, and therefore makes it possible to obtain a high biomass possessing increased metabolic activities towards the membrane lipids. Under these conditions, the synthesis of the phospholipid transfer proteins is increased and is of major industrial interest.

The subject of the present invention is also purified preparations of lipid binding and transfer proteins, characterized:
in that they are capable of ensuring the intermembrane binding, transport and/or rearrangement of lipids, optionally combined with active ingredients,
in that they are capable of being obtained from a crude extract of a non-toxic filamentous fungus, cultured in a phospholipid-rich medium, which fungus is selected from the group comprising the Ascomycetes chosen from *Aspergillus candidus*, *A. flavipes*, *A. fumigatus*, *A. giganteus*, *A. niger*, *A. oryzae*, *A. terreus*, *A. versicolor*, *A. wentii*, *Penicillium roquefortii* and *Eurotium chevalieri*, the Zygomycete *Rhizopus stolonifer* and the Basidiomycete *Phanerochaete chrysosporium*, the said proteins having a specific phospholipid transfer activity expressed in nmol of phosphatidylcholine transferred per minute and per mg of protein greater than or equal to 0.3 nmol/min/mg,
in that they are hydrophobic and acidic, and
in that they have a molecular weight of less than 50 kDa.

These acidic proteins of fungal origin make it possible, because of their capacity for intermembrane binding, transport and transfer of lipids (phospholipids and sterols), to improve, surprisingly, the biological and surfactant activities of the cellular membranes and the biomembranes.

According to an advantageous embodiment of the invention, the said purified preparations of proteins are capable of being obtained preferably from the filamentous fungus strain *A. oryzae*.

According to an advantageous feature of this embodiment, the said acidic lipid transfer proteins have a molecular weight of about 19 kDa.

According to another advantageous feature of this embodiment, the said acidic lipid transfer proteins have a molecular weight of about 30 kDa.

Both the 19 kDa protein and the 30 kDa protein are active for the transfer of lipids; the 30 kDa protein is however more active than the 19 kDa protein for the transfer of phosphatidylcholine.

In accordance with the invention, such PLTPs ensure the specific and preferential transport of phosphatidylglycerol and phosphatidylinositol; as regards the other phospholipids, the order for the level of transfer of phospholipids is the following: phosphatidylcholine>phosphatidylethanolamine>phosphatidylserine.

Such proteins find application in pharmacy, cosmetology and in the agri-foodstuffs field, combined with lipids and preferably with liposomes. They are advantageously combined with the latter, either in an external phase or in an internal phase, or in an encapsulated form.

Generally, such lipid binding and transfer proteins, also called protein shuttles, improve the efficacy of action of liposomes, by their use as "natural vectors" of phospholipids and other hydrophobic molecules, in all the applications of the latter.

In the drug field, the shuttle proteins in accordance with the invention constitute vectors of active ingredients and make it possible to select the cells to be reached.

In the agri-foodstuffs field, these proteins permit, in particular, the valorization of soya bean lecithins (principal sources of phospholipids).

The subject of the present invention is also crude filamentous fungus extracts characterized in that they are capable of being obtained from a non-toxic filamentous fungus by:

(a) culturing the said fungi in a phospholipid-rich medium until a sufficient quantity of mycelium is obtained,
(b) grinding the said mycelia in an extraction buffer at neutral pH,
(c) separating the crude extract containing the lipid binding and transfer proteins from the said ground product by
centrifugation of the said ground product at a speed above 20,000 g (first centrifugation) and recovery of the supernatant S1,
acid precipitation of the supernatant S1, followed by a centrifugation at a speed above 20,000 g (second centrifugation) and recovery of the supernatant S2,
(d) preparing the crude extract containing the said lipid binding and transfer proteins from the supernatant S2 buffered to an essentially neutral pH.

According to an advantageous feature of this embodiment, step (a) includes:
culturing the said fungi on a natural sporulation medium,
incubating for 2 to 13 days until a sufficient quantity of spores is obtained,
culturing the said spores on a phospholipid-rich culture medium, and
incubating until a sufficient quantity of mycelium is obtained.

According to an advantageous aspect of this feature, the sporulation medium advantageously consists of moistened whole maize grains.

In addition to the preceding features, the invention also comprises other features which will emerge from the description below, which refers to exemplary embodiments of the method which is the subject of the present invention.

It should be understood, however, that these examples are given solely by way of illustration of the subject of the invention and do not constitute in any manner a limitation thereto.

EXAMPLE 1

Preparation of a Crude Extract Containing the LTPs

1. Principle.

The following steps consist in extracting the proteins after grinding the mycelium obtained by culturing in a phospholipid-rich medium, and in assaying the phospholipid transfer activity of the extract by fluorescence spectrometry, with the aid of liposomes which are donors of fluorescent probes and unlabelled acceptor liposomes.

2. Selected strains.

Fifteen strains of moulds belonging to the classes of Zygomycetes (order of the Mucorales), Ascomycetes and Basidiomycetes were selected.

These strains were obtained from and are the property of the INRA Laboratory of Cereal Microbiology and Technology (LMTC) at Nantes, the Fungus Culture Collection of the Catholic University of Louvain (MUCL, Belgium) and the INRA Laboratory of Filamentous Fungus Biotechnology (LBCF) at Marseille. Their list is given below.

* Ascomycetes:
Eurotium chevalieri
Anamorphic species:

Aspergillus candidus
A. flavipes
A. fumigatus
A. giganteus

-continued

A. niger
A. ochraceus
A. oryzae
A. terreus
A. versicolor
A. wentii
Penicillium roquefortii
* Zygomycetes:      Mucor mucedo
                    Rhizopus stolonifer
* Basidiomycete:     Phanerochaete chrysosporium 3. Preparation of the inocula and carrying out of the cultures.

The strains are cultured in the laboratory on a natural medium, namely on whole maize grains moistened for 48 hours at 4° C. (on average 40 grains per 100 ml flask) and sterilized for twice 30 min at 110° C. The incubation is performed at 25° C. for 10 to 13 days (maximum). During this period, the mycelium develops at the surface of the grains, producing spores.

These spores are detached from the surface of the grains by shaking glass beads (diameter of 3 mm) bathing in a sterile solution of Tween 80° at 0.033 g/l (so as to avoid flocculation of the spores). The spore suspension thus obtained is filtered on glass wool so as to remove the mycelial fragments and the grain debris.

An enumeration is carried out on a Malassez cell. The inoculum for the cultures can then be quantified using an aliquot of known volume of the spore solution. The concentration of the stock solution is in general of the order of $2*10^7$ spores/ml.

Two other sporulation media were tested with A. oryzae: soya bean grains (high in phospholipids) moistened and sterilized for twice 30 min at 110° C. and a synthetic medium (MYA2) composed of solid malt (20 g/l), yeast extract (1 g/l) and agar (13 g/l) sterilized in an autoclave for 20 min at 120° C.

100 ml of culture medium (composition detailed below) are used in baffle flasks of 500 ml capacity. These media are inoculated with spores in an amount of $2*10^5$ spores/ml. The cultures are incubated at 25° C. and subjected to a rotary shaking of 120 rotations/min for 3 days. At the end of this incubation period, the mycelium is filtered on sintered glass (no. 2), weighed and then frozen at -20° C.

| * Composition of the culture medium: | |
|---|---|
| $KH_2PO_4$ | 0.2 g/l |
| $MgSO_4.7H_2O$ | 0.5 g/l |
| $CaCl_2.2H_2O$ | 0.0132 g/l |
| Ammonium tartrate | 1.84 g/l |
| Yeast extract | 0.5 g/l |
| Source of phospholipids | 3–20 g/l |

The source of phospholipids is preferably a mixture of phospholipids depleted of phosphatidylcholine.

* Preparation:

It is carried out using the following volumes:
50 ml of sterile distilled water,
10 ml of stock solution 1: $KB_2PO_4$ 2 g/l, $MgSO_4.7H_2O$ 5 g/l, $CaCl_2.2H_2O$ 0.132 g/l, autoclaved in a flask for 20 min at 120° C. and stored at 4° C.,
10 ml of stock solution 2: ammonium tartrate 18.4 g/l autoclaved for 20 min at 120° C. and stored at 4° C.,
10 ml of stock solution 3: yeast extract 5 g/l, autoclaved for 20 min at 120° C. and stored at 4° C., 20 ml of stock solution 4: Nat 89 at 50 g/l, prepared using an ultrasound bath, and then stirred. The solution is then autoclaved for 20 min at 120° C. and stored at 4° C.

4. Preparation of the crude extract.

2 grams of mycelium (fresh weight) are ground at 0° C. in the presence of about 2 g of Fontainebleau sand in a mortar with the aid of a pestle. The sand was washed with a HCl solution, rinsed several times with water and then sterilized at 200° C. for 30 min in a Pasteur oven.

The grinding is carried out in a buffer containing a 100 mM Tris-HCl solution pH 7.0, supplemented with 2 mM EDTA (cation-dependent protease inhibitor), 400 mM sucrose (osmotic protecting agent), 2 mM dithiotkreitol and 8 mM 2-mercaptoethanol (reducing agents).

The following steps (centrifugations and preparation of the crude extract ) are described in FIG. 1.

The acid precipitation at pH 5.1 offers the advantage of freeing the phospholipid transfer proteins of soluble lipoprotein complexes which interfere with the phospholipid transfer assays.

In the final step, the pH is adjusted to 7.8 in order to stabilize the proteins.

5. Detection of the presence of the lipid transfer proteins.

a) Principle.

The measurements of transfer are carried out by monitoring the increase in fluorescence in a dilution buffer after adding a protein solution containing the phospholipid transfer proteins to a mixture of donor liposomes A which are labelled (by a pyrene monomer), blocked by "quenching" effect, and an excess of unlabelled recipient liposomes B.

The "quenching" effect amounts to a decrease or even an inhibition of fluorescence due to a too high concentrating of the probe.

Figure 2:
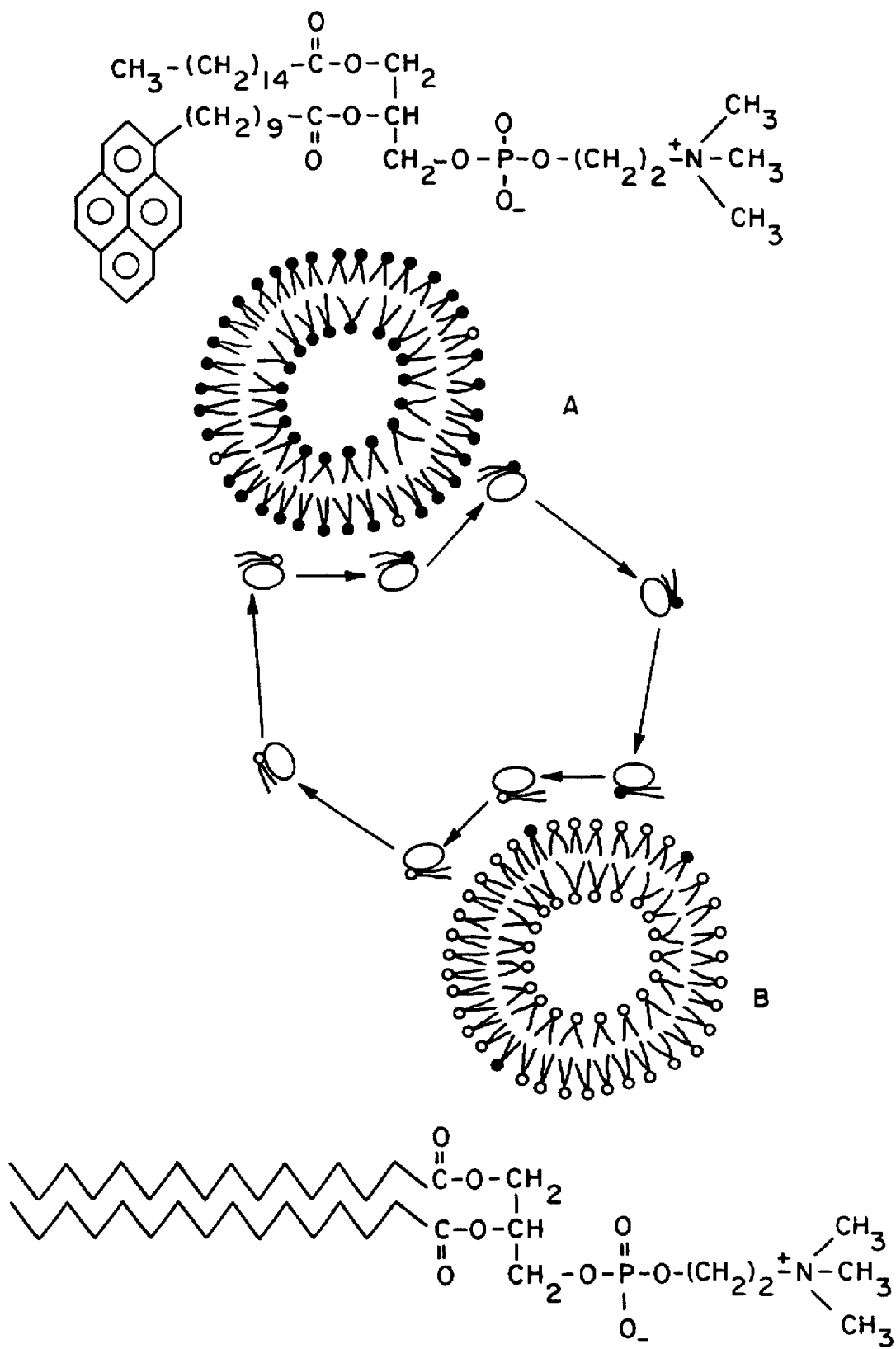
FIG. 2 illustrates the method of phospholipid transfer.

The phospholipid transfer activity is monitored by the movement of the probe between the two populations of liposomes after addition of the fungal protein extract, in accordance to FIG. 2, which illustrates this measurement of phospholipid transfer by means of protein shuttles from a donor liposome A (●) consisting of pyrene phosphatidylcholine (fluorescent probe) to an acceptor liposome B (○) consisting of egg phosphatidylcholine.

b) Equipment:

An SLM 4800 C Aminco spectrofluorimeter (USA) is used for the measurements.

The light source is a xenon lamp. The excitation (Glan Thomson) and emission (polaroid polarizing film) monochromators select the wavelengths of 346 and 378 nm respectively. A measurement corrected for the variations of the lamp is obtained by dividing the emission signal of the solution analyzed by that observed with the reference solution (rhodamine cell). The apparatus is equipped with a cuvette rack thermostated by circulation of water. The spectrofluorimeter is controlled by a microcomputer which permits the acquisition and processing of data.

c) Donor liposomes A:

Reagents: the fluorescent probe used is 3-palmitoyl-2-(1-pyrenedecanoyl)-L-a-phosphatidylcholine (Molecular Probes, USA) with a molecular weight of 852 (see FIG. 2). It is provided in the form of a dry extract of 1.17 μmol/mg in a plastic tube, preserved at −20° C. It has an excitation maximum at 346 nm and an emission maximum at 378 nm.

Preparation: the contents are solubilized in 10 ml of absolute alcohol. This stock solution has a concentration of 117 mM. It is packaged in a volume of 0.5 ml in glass tubes and preserved at −20° C. protected from light.

For the assay, a 10 μl sample makes it possible to have 1.17 nmol of probe in the assay cuvette.

d) Acceptor liposomes B:

Reagent: the preparation of these liposomes is carried out using a solution of egg yolk -Lα-phosphatidylcholine (see FIG. 2) at 100 mg/ml (solubilized in tetradecane (Sigma) and having a molecular weight of 775. The storage is at −20° C.

Preparation: 385 μl of this solution are collected, evaporated for 15 min under a nitrogen stream, then diluted in 10 ml of fluorescence buffer (20 mM Tris-HCl, 5 mM EDTA, 100 mM NaCl, pH 7.4 filtered on 0.45 μMillipore filter) in order to obtain a 5 mM suspension consisting of heterogeneous multilamellar vesicles (MLV).

In order to pass to the unilamellar vesicle stage (SUV), sonication is used. The MLVs are subjected to ultrasound with the aid of a Vibra Cell (Sonic and Materials, Danbury, Conn., USA) provided with a ½ microprobe. The sonication is performed in pulsatory mode with a medium power (position 4) and a cycle proportion of 50%. The operation is carried out for twice 10 min with cooling on an ice bath. The solution obtained is filtered on a 0.2μ Sartorius filter and stored at 4° C.

e) Assay conditions:

The assay is performed in 1.5 ml of fluorescence buffer, with 10 μl of fluorescent probe and 14 μl of liposome solution. The liposome/probe ratio is 60 so as to have an excess of recipient vesicles.

The protein solution (50 μl) is added last so as to start the kinetics of phospholipid transfer between the two liposome populations. The reaction is carried out at 25° C.

f) Measurement conditions:

The fluorescence measurements are performed in quartz cuvettes of 10 mm over 4 mm of optical path length in emission and excitation modes respectively.

The excitation and emission wavelengths are fixed at 346 and 378 nm respectively (maximum excitation and emission of the fluorescent probe) and the slits of the excitation and emission monochromators at 4 nm.

g) Calculation of the phospholipid transfer activity:

The transfer kinetics are performed over 1400 seconds with recordings of intensity every 5 seconds. The transfer activity is represented by the initial slope of the kinetics (unit of relative fluorescence intensity over time).

The value of the relative transfer activity is calculated in relation to the maximum fluorescence value. This maximum is obtained by adding a 20 % (W/V) SDS solution (50 μl) to the sample. The SDS dissociates the donor liposomes diluting the entire fluorescent probes in the measuring cuvette, it thus suppresses the "quenching" effect. The fluorescence intensity obtained under these conditions therefore corresponds to the quantity of probe injected into the assay (1.17 nmol).

The specific activity is obtained by calculating the ratio of the relative activity over the quantity of proteins which we provided in the assay. The specific activity is expressed in nmol of phosphatidylcholine transferred per minute and per mg of proteins.

6. Results.

a) Selection of strains having a phospholipid transfer activity:

The cultures were harvested at the optimum phospholipid activity (age of the spores obtained from maize grains, 13 days and age of the cultures, 3 days).

Figure 3:
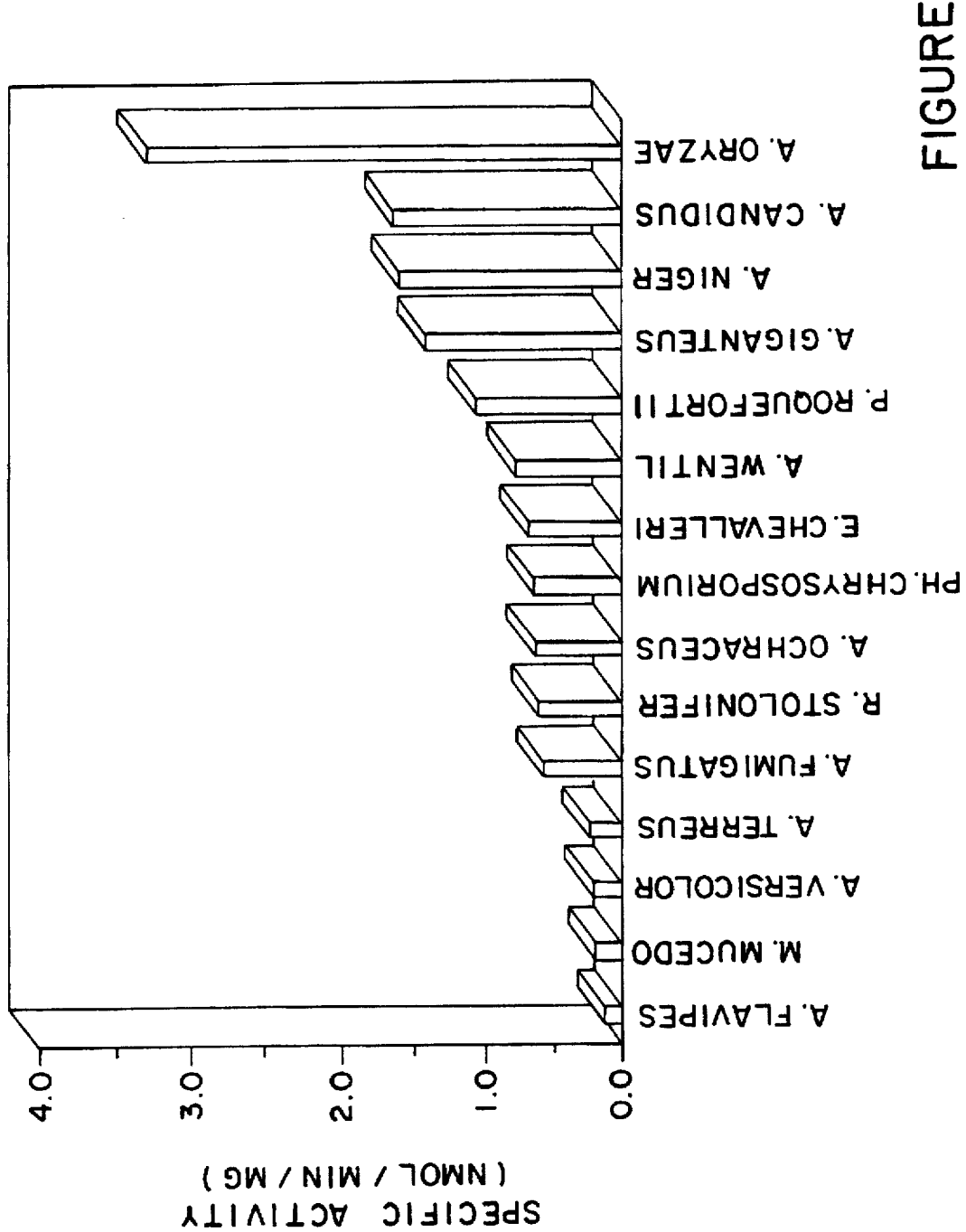
FIG. 3 illustrates the specific activity (nmol of phosphatidylchloine transferred/min/mg) of various strains.

All the tested strains show a phospholipid transfer activity but with, however, a strain which is found to be clearly more efficient (FIG. 3). It is *Aspergillus oryzae* which has an activity which is twice as high as *A. candidus* or *A. niger*.

FIG. 3 illustrates the specific activity (nmol of phosphatidylcholine transferred/min/mg) in various strains.

b) Comparison of the quality of various inocula:

A purely synthetic medium and a natural medium (soya bean seeds) known for their high phospholipid content were tested in addition to the maize grains.

A maximum phospholipid transfer activity is observed within three days of culture for *A. oryzae* obtained from an inoculum of maize grains. From the second day, the activity is detected and it decreases beyond three days to four days (FIGS. 4 and 5).

Figure 4:
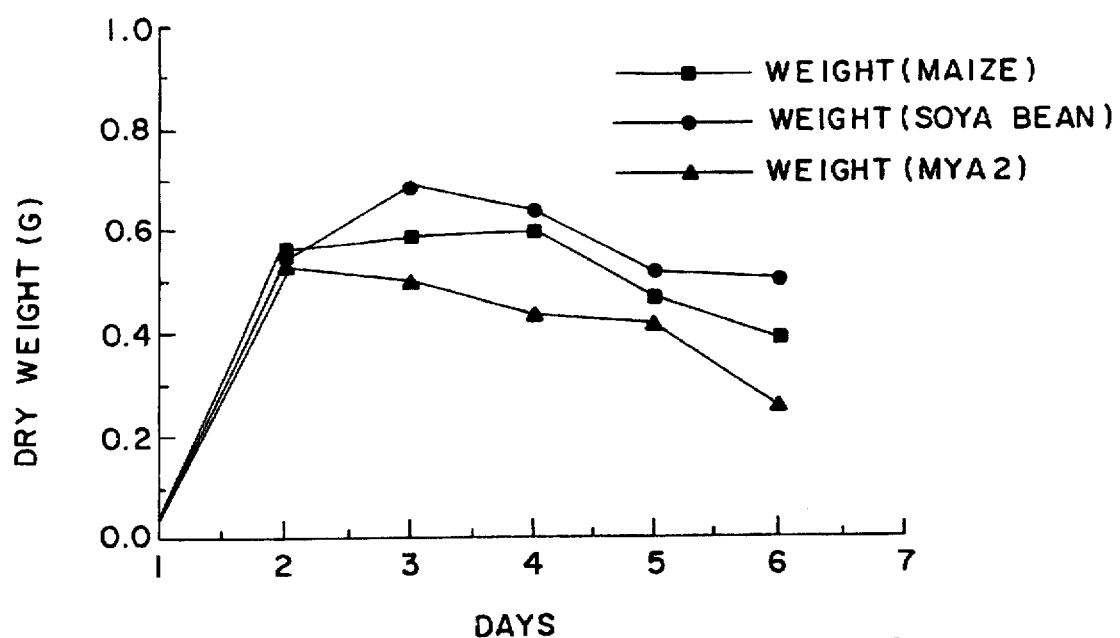
FIG. 4 illustrates the growth A. oryzae obtained from various inocula.

FIG. 4 illustrates the growth of *A. oryzae* obtained from various inocula (—■—: maize; —●—: soya bean; —▲—: MYA2) and comprises on the x-axis the number of days of culture and on the y-axis the dry weight (in g) of *A. oryzae*.

Figure 5:
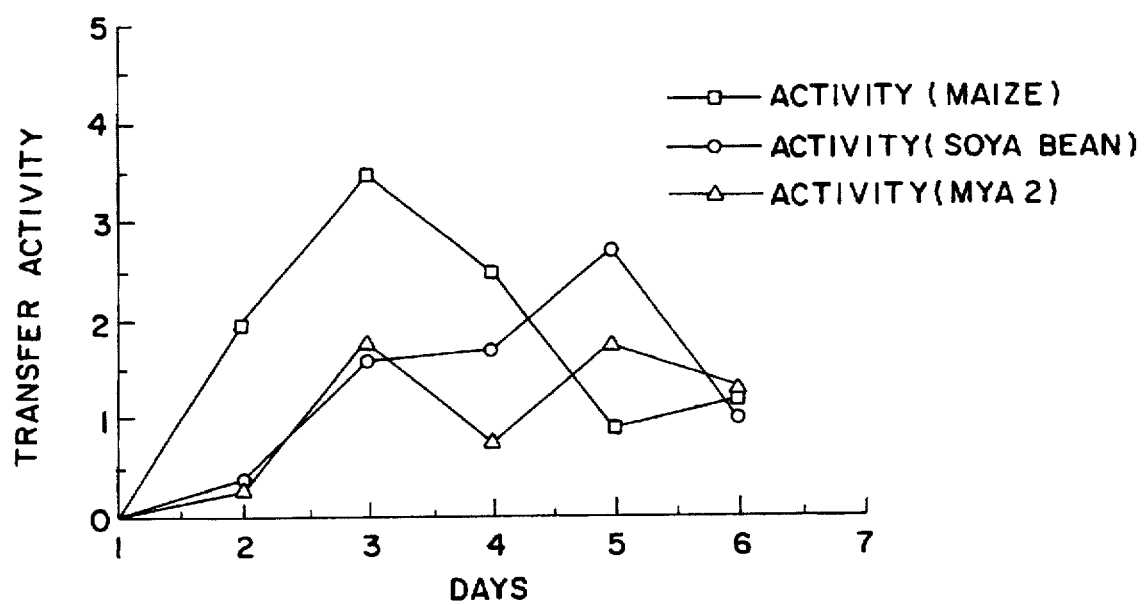
FIG. 5 illustrates the phospholipid transfer activity of A. oryzae obtained from various inocula.

FIG. 5 illustrates the phospholipid transfer activity of *A. oryzae* obtained from various inocula and comprises on the x-axis the number of days and on the y-axis the transfer activity of inocula cultured on maize (—□—, soya bean (—○—) or synthetic medium (MYA2) (—△—).

The maximum transfer activity for *A. oryzae* obtained from an inoculum of spores on synthetic medium is at three days as observed on maize grains, but it is half lower. The activity then tends to decrease but less sharply (FIGS. 4 and 5).

The transfer activity of *A. oryzae* obtained from an inoculum of spores on soya bean seeds is at its maximum later, at five days. The activity is then slightly lower than with maize as inoculum (FIGS. 4 and 5).

In conclusion, the maximum phospholipid transfer activity is obtained with *A. oryzae* obtained from an inoculum on maize grains. The spores obtained from the maize inoculum also respond more rapidly to the needs of the cell.

EXAMPLE 2

Purification and Characterization of The Proteins

1) Purification:

The proteins are purified from the crude extract as obtained in Example 1, as schematically represented in FIG. 6.

For that, 900 g of mycelium (wet weight) are ground in 3 liters of extraction buffer (100 mM Tris-HCl, pH 7.0, 2 mM EDTA, 2 mM dithiothreitol, 8 mM 2-mercaptoethanol, 400 mM sucrose).

The proteins of the crude extract are concentrated (supernatant of the acid precipitation at pH 5.1) by ultrafiltration.

The membrane used for concentrating the crude extract (supernatant of the precipitation at pH 5.1) is a Millipore Pelicon® PLGC membrane. It has a molecular weight cut-off of 10 kDa and a surface area of 0.1 m$^2$; such an ultrafiltration makes it possible to concentrate the extract and remove all proteins with a molecular weight of less than 10 kDa.

Such a technique has, in addition, the advantage of causing negligible loss of protein; this is important especially when the initial concentration of protein is less than 1 mg/ml.

The purification itself comprises several steps, and at each step, there is:
checking of the transfer activity,
polyacrylamide gel electrophoresis in the presence of sodium dodecyl sulphate,
assay of the proteins.

*1st purification step:
Gel filtration on Sephadex G75® column (2.6×100 cm) equilibrated with the buffer B: 50 mM Tris, 8 mM 2-mercaptoethanol, 200 mM NaCl, 10% (w/v) glycerol pH 7.8, with a flow rate of 15 ml/hour. 5 ml fractions are collected. The elution profile is shown in FIG. 7(A) or FIG. 8(A) and comprises 2 activity peaks: P1 and P2. The active fractions are separately assembled: fractions 38 to 52 for P1 and 62 to 79 for P2.

*2nd purification step: DEAE-Sephacel® (FPLC).

Both fractions (about 300 ml) obtained from the Sephadex chromatography are loaded onto a 2.6×15 cm DEAE-Sephacel® column after ½ dilution for P2 (in order to reduce the ionic strength). The column is previously equilibrated with the buffer A. The column is eluted until the optical density returns to the base, so as to remove all the unbound proteins:

a) the P1 proteins are eluted with 200 ml of a linear gradient (200–700 ml NaCl).

b) the P2 proteins are eluted with 350 ml of a linear gradient (100–500 ml NaCl).

The flow rate is 30 ml/hour and the fractions collected 5 ml.

The transfer activities corresponding to P1 and P2 are eluted with fractions 23–36 (about 500 nM NaCl) and fractions 51–61 (about 350 mM NaCl) respectively.

Figure 7:
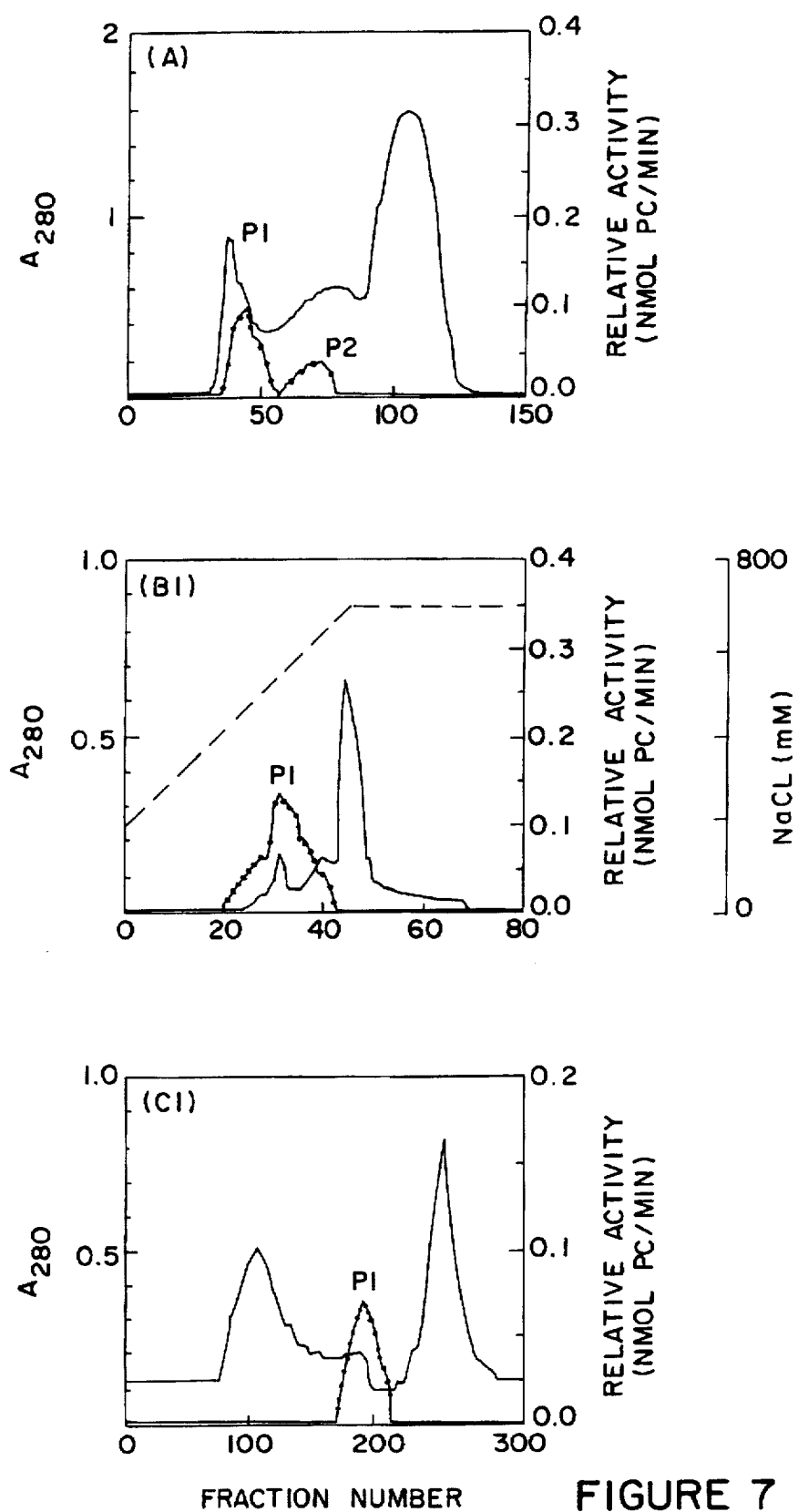
FIGS. 7(A, B1 and C1) shows the elution profiles of purified protein.

*3rd purification step:

3a. Sephacryl® S400 chromatography. 166 ml of the P1 fraction which are obtained from the DEAE are loaded onto a Sephacryl® S400 column (4.5×85 cm) equilibrated with the buffer B. The flow rate is 60 ml/hour and the fractions collected 5 ml. FIG. 7(C1) shows the profile with an activity peak for fractions 185 to 204.

3b. MonoQ® chromatography (FPLC). 30 ml of P2 which are obtained from the DEAE are loaded onto a MonoQ® HR 515 column equilibrated with the buffer A. The elution of the active protein is performed with 40 ml of a linear gradient of 0 to 500 mM NaCl in the same buffer. The flow rate is 60 ml/hour and the fractions collected 2 ml. The phospholipid transfer activity is detected for about 120 mM NaCl.

Molecular mass: a 30 kDa band corresponding to the P1 fraction is observed on polyacrylamide gel. A 19 kDa band is observed for the P2 fraction.

Figure 8:
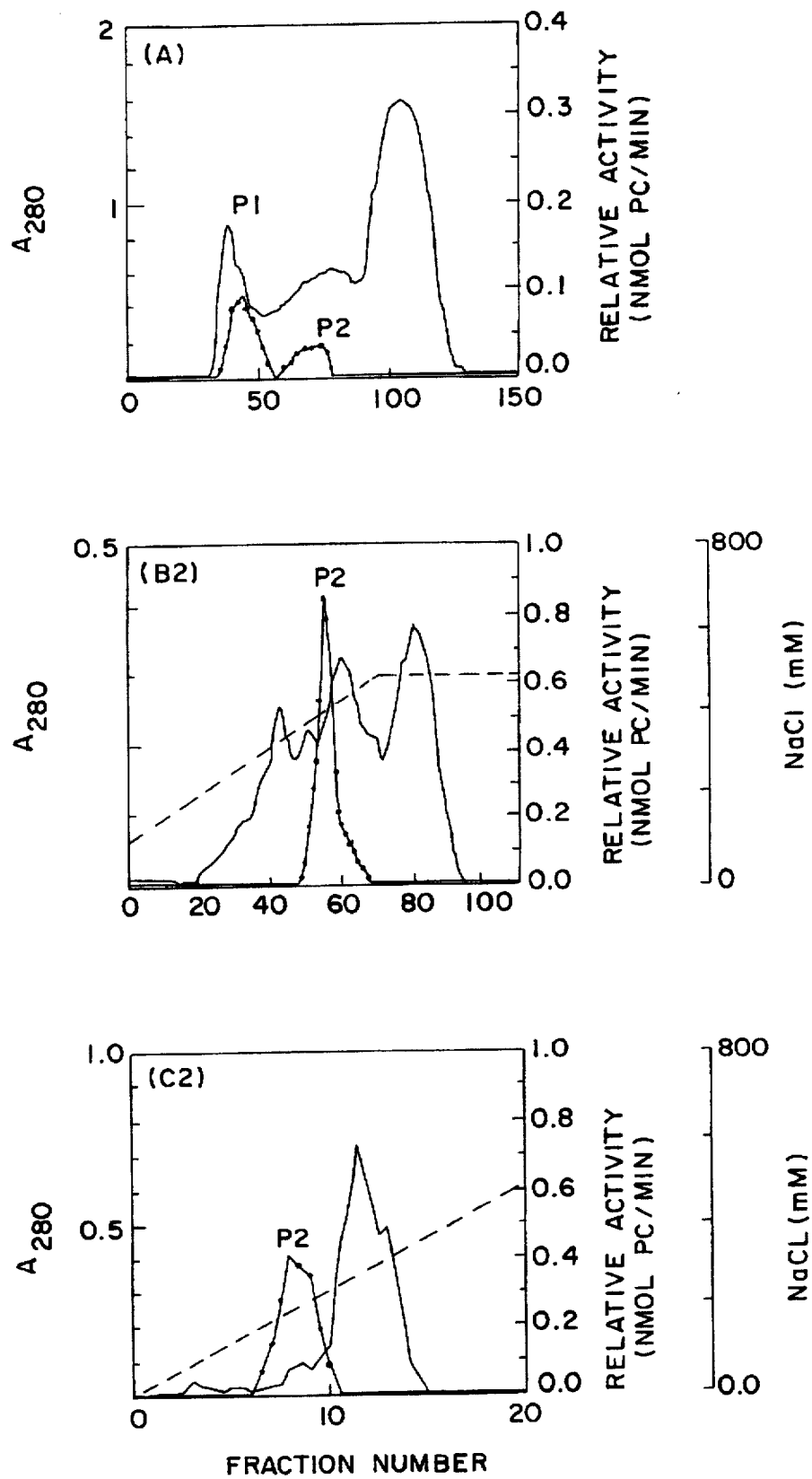
FIGS. 8(A, B2 and C2) shows the elution profiles of purified protein.

FIGS. 7 and 8 illustrate these various purification steps for the P1 peak (FIG. 7) and the P2 peak (FIG. 8) and comprise on the x-axis the fraction numbers and on the y-axis the absorbance at 280 nm (left-hand axis and continuous line) and the phospholipid transfer activity, measured on aliquots (▲) and expressed in nmol of phosphatidylcholine/min (right-hand axis). The NaCl gradient (mM) is established by measurement of conductivity (broken line).

FIGS. 7(A) and 8(A) are equivalent and correspond to gel filtration on a Sephadex® G75 column.

FIGS. 7(B1) and 7(C1) illustrate the 2nd and 3rd purification steps for the P1 peak (DEAE column, gradient 200–700 mM and Sephacryl® S400).

FIGS. 8(B1) and 8(C1) illustrate the 2nd and 3rd purification steps for the P2 peak (DEAE column, gradient 100–500 mM and MonoQ®, gradient 100–500 mM).

2) Characterization of the phospholipid transfer proteins: Molecular specificity:

The molecular specificity is determined by fluorescence with the aid of fluorescent probes (pyrene) as in Example 1. The donor and acceptor liposomes are prepared by injecting an ethanolic solution of phospholipids into an appropriate buffer, following the G. LAFER method (Biochimica et Biophysica Acta, 1991, 1069, 139–144).

The proteins in accordance with the invention and especially those obtained from *A. oryzae* have the novelty of transporting more specifically phosphatidylglycerol and phosphatidylinositol. In the decreasing order of preference, they also transport: phosphatidylglycerol>phosphatidylinositol>phosphatidyl choline>phosphatidylethanolamine>phosphatidylserine.

N-terminal sequence of the 19 kDa protein obtained from *A. oryzae*:

This sequence was determined according to the Edman method with the Applied Biosystem 470A apparatus. The amino acid sequence shows no homology with other PLTPs:

$H_2N$-Ala-Lys-Ser-Val-Pro-Gly-Asn-Asn-Pro-Leu-Glu-Tyr-

Cys-Asn-Asp-Pro-Ser-Gly-Asp-Ile-Leu-Asp-Ile-Lys-Gln-

Val-Asp-Leu-Ser-Pro-Asn-Pro.(SEQ ID NO: 1)

Isoelectric point:

The isoelectric point was determined with the Pharmacia Phast-system. The 19 kDa protein has a pH of 4.8.

Resistance of the protein to heat:

The pure 19 kDa PLTP is heated for 10 min at 100° C. and then cooled on ice before assaying the phospholipid transfer activity. The results obtained indicate that the protein is stable after this treatment.

Specific activity

With a crude extract (supernatant of the acid precipitation at pH 5.1), there is an activity of 3.3 mmol/min/mg, equivalent to 198 nmol/h/mg with *Aspergillus oryzae*. After purification, there is, for the pure 19 kDa protein, an activity of 20,000 nmol/h/mg.

Figure 9:
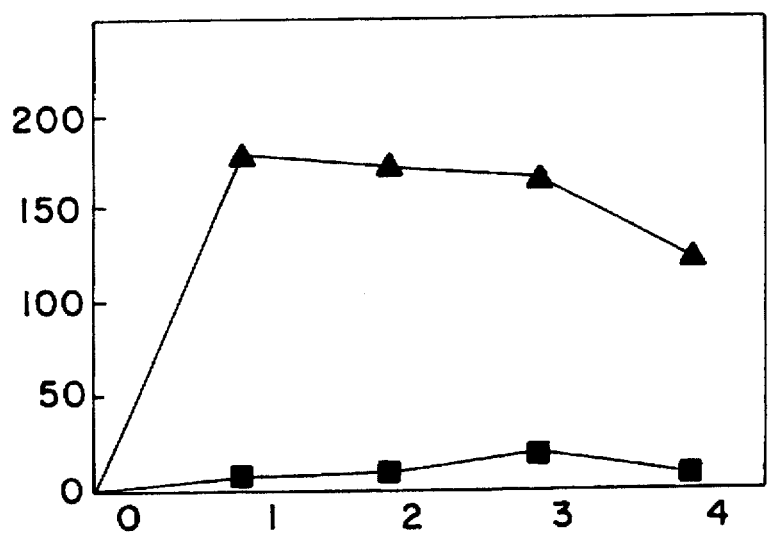
FIG. 9 illustrates the activity of the endoplaemic reticulum of a fungus cultured in a glucose-based liquid medium or in a phospholipid-rich liquid medium.

From the first day, a very high stimulation of the activity of the endoplasmic reticulum (site of phospholipid synthesis) is noted when the fungus is cultured on phospholipid-rich medium (FIG. 9, curve ▲).

Figure 10:
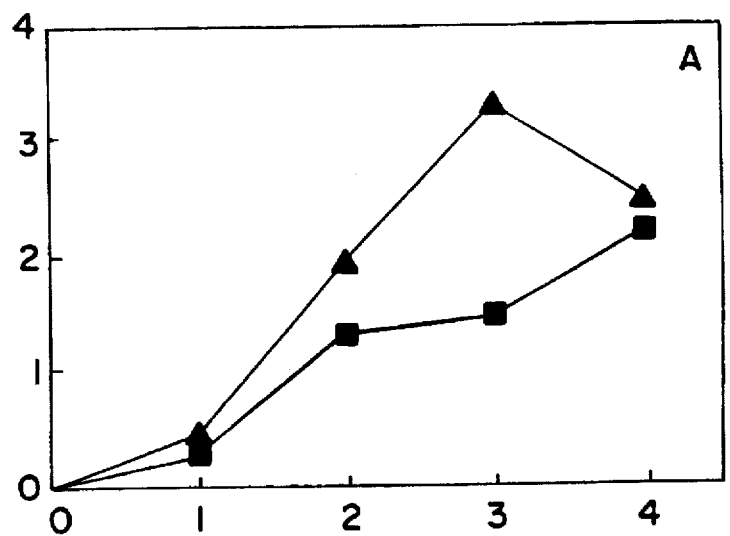
FIG. 10 illustrates phospholipid transfer activity obtained after culturing in a glucose-based liquid medium or in a phospholipid-rich liquid medium.

In parallel, the phospholipid transfer activity is illustrated in FIG. 10 which comprises on the y-axis the phosphatidylcholine transfer activity expressed in $nmol.min^{-1}.mg^{-1}$ of intracellular protein and on the x-axis the duration of incubation in days. The curve (■) illustrates the transfer activity obtained after culturing in a glucose-based medium and the curve (▲) illustrates the transfer activity obtained after culturing in a phospholipid-based medium; this FIG. 10 indeed shows a significantly higher stimulation of the transfer in the presence of phospholipids (curve ▲) compared to a culture on glucose (curve ■): indeed, this figure indeed shows that, at 3 days, the transfer activity from a phospholipid-rich medium is twice higher.

As is evident from the above, the invention is not in any way limited to its embodiments, implementation and applications which have just been described more explicitly; it embraces on the contrary all the variants which may occur to a specialist in this field, without departing from the framework or the scope of the present invention.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 32 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:1:

```
Ala Lys Ser Val Pro Gly Asn Asn Pro Leu Glu Tyr Cys Asn Asp Pro
  1               5                  10                  15

Ser Gly Asp Ile Leu Asp Ile Lys Gln Val Asp Leu Ser Pro Asn Pro
             20                  25                  30
```

EXAMPLE 3

Role of the Phospholipid-Rich Culture Medium in the Stimulation of the Endoplasmic Reticulum and in the Increase in the Production of the Phospholipid Transfer Proteins:

Comparison with a culture on glucose-based medium

The activity of the endoplasmic reticulum of a fungus cultured in a glucose-based liquid medium (FIG. 9, curve ■) or in a phospholipid-rich medium (FIG. 9, curve ▲) is compared by assaying the enzymatic activity of the cytochrome C oxydoreductase (specific marker for the reticulum) according to the R. L. JONES method (1980, Planta, 150, 58–69). In FIG. 9, the y-axis corresponds to the cytochrome C oxydoreductase activity expressed in $nmol.min^{-1}.mg^{-1}$ of intracellular protein and the x-axis corresponds to the incubation time in days.

We claim:

1. A method for preparing phospholipid transfer proteins (PLTP) from non-toxic filamentous fungi, comprising culturing non-toxic filamentous fungi in a phospholipid-rich medium, preparing a crude extract from said cultured fungi, separating the proteins from the said extract, and purifying said proteins, wherein the phospholipid-rich medium comprises between 3 and 20 g/l of phospholipid, as a carbon source.

2. A method for preparing phospholipid transfer proteins (PLPT) from non-toxic filamentous fungi, comprising:

(1) preparing a crude extract at an essentially neutral pH by:
      (a) culturing non-toxic, filamentous fungi in a phospholipid-rich medium comprising between 3 and 20 g/l of phospholipid as a carbon source until a sufficient quantity of mycelia is obtained, (b) grinding said mycelia in an extraction buffer at neutral pH to obtain a round product, (c) separating the crude extract containing said phospholipid transfer proteins (PLTP) from said ground product, by:

a first centrifugation of said ground product at a speed above 20,000 g and recovery of a first supernatant S1, acid precipitation of said supernatant S1, followed by a second centrifugation at a speed above 20,000 g and recovery of a second supernatant S2, (d) recovering the crude extract containing said phospholipid transfer proteins (PLTP) from the second supernatant S2, buffered to an essentially neutral pH, (2) concentrating said phospholipid transfer proteins (PLTP) by ultrafiltration, (3) separating fractions having a phospholipid transfer activity, and (4) purifying proteins of various fractions selected, by a series of chromatographic steps.

3. The method for preparing phospholipid transfer proteins (PLTP) according to claim 2, wherein said filamentous fungi are selected from the group consisting of (i) Ascomycetes selected from *Aspergillus candidus, A. flavipes, A. fumigatus, A. giganteus, A. niger, A. ochraceus, A. oryzae, A. terreus, A. versicolor, A. wentii, Penicillium roquefortii* and *Eurotium chevalieri*, (ii) Zygomycetes selected from *Mucor mucedo* and *Rhizopus stolonifer* and (iii) Basidiomycetes selected from the species *Phanerochaete chrysosporium*.

4. The method for preparing phospholipid transfer proteins (PLTP) according to claim 2, wherein steps (b), (c) and (d) are performed at cold temperature.

5. A method for transporting intermembrane phospholipid, comprising obtaining proteins according to claim 2, and using said proteins to transport intermembrane phospholipid.

6. A composition comprising a purified preparation of phospholipid transfer proteins (PLTP), wherein:

the proteins are effective for ensuring the intermembrane binding, transport and/or rearrangement of lipids, the proteins are capable of being obtained from a crude extract of *A. oryzae* fungus, cultured in a phospholipid-rich medium, comprising between 3 and 20 g/l of phospholipid as a carbon source said proteins having a molecular weight of about 19 kDa or a molecular weight of about 30 KDa on SDS-PAGE, the 19 kDa protein having a phospholipid transfer specific activity expressed in nmol of phosphatidylcholine transferred per hour and per mg of protein of about 20,000 nmol/h/mg, the proteins being hydrophobic and acidic.

7. The composition comprising purified preparation of proteins according to claim 6, wherein said proteins of about 19 kDa has the following N-terminal amino acid sequence recited in SEQ. ID. NO. 1:

H$_2$N—Ala—Lys—Ser—Val—Pro—Gly—Asn—Asn—Pro—Leu—Glu—Tyr—Cys—Asn—Asp—Pro—Ser—Gly—Asp—Ile—Leu—Asp—Ile—Lys—Gln—Val—Asp—Leu—Ser—Pro—Asn—Pro and has an isoelectric point of about 4.8.

8. A composition comprising a crude filamentous fungus extract wherein said extract is capable of being obtained from *A. oryzae* fungus by:

(a) culturing said *A. oryzae* in a phospholipid-rich medium comprising between 3 and 20 g/l of phospholipid at 25° C., under a rotary shaking of 120 rotations/min until a sufficient quantity of mycelia is obtained, (b) grinding the said mycelia in an extraction buffer at neutral pH to obtain a ground product, (c) separating the crude extract containing the phospholipid transfer proteins from said ground product by:

a first centrifugation of the said ground product at a speed above 20,000 g and recovery of a first supernatant S1, acid precipitation at pH 5.1 of said supernatant S1, followed by a second centrifugation at a speed above 20,000 g and recovery of a supernatant S2, (d) recovering the crude extract containing said phospholipid transfer proteins from the supernatant S2 buffered to an essentially neutral pH, said crude extract having phospholipid transfer activity expressed in nmol of phosphatidylcholine transferred per minute and per mg of protein greater than or equal to 0.3 nmol/min/mg.

9. The composition comprising a crude extract according to claim 8, wherein step (a) further comprises:

culturing said *A. oryzae* on a sporulation medium, consisting of whole maize grains, incubating for 2 to 13 days until a sufficient quantity of spores is obtained, culturing said spores on said phospholipid-rich culture medium, and incubating until a sufficient quantity of mycelia is obtained.

10. A method for preparing phospholipid transfer proteins (PLTP) from non-toxic filamentous fungi comprising:

(1) preparing a crude extract at an essentially neutral pH by:

(a) culturing non-toxic, *Aspergillus oryzae* fungi in a phospholipid-rich medium comprising between 3 and 20 g/l of phospholipid at 25°, under a rotary shaking of 120 rotations/min until a sufficient quantity of mycelia is obtained, (b) grinding said mycelia in an extraction buffer at neutral pH to obtain a ground product, (c) separating the crude extract containing said phospholipid transfer proteins (PLTP) from said ground product, by:

a first centrifugation of said ground product at a speed above 20,000 g and recovery of a first supernatant S1, acid precipitation at pH 5.1 of said supernatant S1, followed by a second centrifugation at a speed above 20,000 g and recovery of a second supernatant S2, (d) recovering the crude extract containing said phospholipid transfer proteins (PLTP) from the supernatant S2, buffered to an essentially neutral pH, (2) concentrating said phospholipid transfer proteins (PLTP) by ultrafiltration (3) separating fractions having a phospholipid transfer activity and (4) purifying proteins of various fractions selected, by a series of chromatographic steps.

11. The method according to claim 10, wherein step (a) further comprises:

culturing said *A. oryzae* on a sporulation medium consisting of whole maize grains, incubating for 2 to 13 days until a sufficient quantity of spores is obtained, culturing said spores on said phospholipid-rich culture medium, and incubating until a sufficient quantity of mycelia is obtained.

12. The method for preparing phospholipid transfer proteins (PLTP) according to claim, 10, wherein said proteins having a phospholipid transfer activity have a molecular weight of about 19 kDa, on SDS-PAGE.

13. The method for preparing phospholipid transfer proteins (PLTP) according to claim 10, wherein said protein having a phospholipid transfer activity has a molecular weight of about 30 kDa, on SDS-PAGE.

14. A composition comprising a modified biomembrane wherein said biomembrane is capable of being obtained by modifying its lipid structure with the aid of phospholipid transfer proteins obtained according to claim 10.

15. A pharmaceutical composition comprising a hydrophobic active ingredient combined with the phospholipid transfer proteins which are obtained according to claim 10.

16. A cosmetic composition comprising uni or multilamellar liposomes, combined with the phospholipid transfer proteins which are obtained according to claim 10.

17. The method for preparing phospholipid transfer proteins (PLTP) according to claim 10, wherein steps (b), (c) and (d) are performed at cold temperature.

* * * * *

UNITED STATES PATENT AND TRADEMARK OFFICE
CERTIFICATE OF CORRECTION

PATENT NO. : 5,717,070
DATED : February 10, 1997
INVENTOR(S) : Record et al.

It is certified that error appears in the above-indentified patent and that said Letters Patent is hereby corrected as shown below:

In column 13, line 2, delete the word "round" and insert the word --ground--.

In column 15, line 2, after the word "claim" delete ",".

In column 13, line 44, after the word "phospholipid" insert a comma --,--.

In column 13, line 52, after "comprising" insert --a--.

In column 13, line 54, change "has" to --have--.

In column 14, line 1, after "grinding" delete "the".

In column 14, line 13, after "having" insert --a--.

Signed and Sealed this

Twenty-eighth Day of April, 1998

Attest:

*Attesting Officer*

BRUCE LEHMAN

*Commissioner of Patents and Trademarks*